United States Patent [19]

Rose et al.

[11] Patent Number: 4,976,742

[45] Date of Patent: Dec. 11, 1990

[54] META-AMINOPHENOLS USEFUL AS OXIDATION HAIR DYE COUPLERS

[75] Inventors: David Rose, Hilden; Edgar Lieske, Duesseldorf; Norbert Maak, Neuss, all of Fed. Rep. of Germany

[73] Assignee: Henkel Kommanditgesellschaft auf Aktien, Duesseldorf-Holthausen, Fed. Rep. of Germany

[21] Appl. No.: 191,722

[22] Filed: May 6, 1988

Related U.S. Application Data

[63] Continuation of Ser. No. 878,557, Jun. 26, 1986, abandoned.

[30] Foreign Application Priority Data

Jul. 8, 1985 [DE] Fed. Rep. of Germany ....... 3524329

[51] Int. Cl.$^5$ .................... A61K 7/13; C07C 211/00
[52] U.S. Cl. ............................ 8/412; 8/421; 564/442
[58] Field of Search ............... 564/442; 8/412, 421

[56] References Cited

U.S. PATENT DOCUMENTS

| | | | |
|---|---|---|---|
| 3,591,323 | 6/1971 | Kalopissis et al. | 564/442 |
| 3,893,803 | 7/1975 | Kaiser | 8/421 |
| 4,031,160 | 6/1977 | Kalopissis et al. | 564/442 |
| 4,065,255 | 12/1977 | Andrillon et al. | 8/412 |
| 4,101,576 | 7/1978 | Kalopissis et al. | 564/167 |

FOREIGN PATENT DOCUMENTS

| | | |
|---|---|---|
| 0039030 | 4/1981 | European Pat. Off. |
| 0023257 | 6/1981 | European Pat. Off. |
| 1543808 | 12/1969 | Fed. Rep. of Germany |
| 2509152 | 9/1976 | Fed. Rep. of Germany |
| 2628641 | 1/1977 | Fed. Rep. of Germany |
| 3016008 | 10/1981 | Fed. Rep. of Germany |
| 1100219 | 12/1966 | United Kingdom |
| 1530686 | 11/1978 | United Kingdom |

OTHER PUBLICATIONS

Chemical Abstracts, vol. 20, No. 21, Nov. 10, 1926.
Journal of Chemical Society, (1926), pp. 2036–2038.
Beilstein's Handbook of Organic Chemistry, 4.Aufl. 2.Erg-Werk, Bd XIII.

*Primary Examiner*—Glennon H. Hollrah
*Assistant Examiner*—Scott C. Rand
*Attorney, Agent, or Firm*—Ernest G. Szoke; Wayne C. Jaeschke; Norvell E. Wisdom, Jr.

[57] ABSTRACT

Meto-aminophenols of the formula

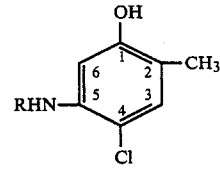

where R is hydrogen, $C_{1-4}$-alkyl, or a $C_{2-4}$-hydroxyalkyl; and their use as couplers in an oxidative hair dye in combination with developers.

16 Claims, No Drawings

META-AMINOPHENOLS USEFUL AS OXIDATION HAIR DYE COUPLERS

This application is a continuation of application Ser. No. 878,557, filed June 26, 1986 now abandoned.

BACKGROUND OF THE INVENTION

1. Field of the Invention

This invention relates to new m-aminophenols and water-soluble salts thereof. These compounds are particularly suitable for use as couplers in oxidation hair dyes.

2. Statement of Related Art

By virtue of their intense colors and good fastness properties, oxidation hair dyes, which are formed by the oxidative coupling of one or more developer components with one another or with one or more coupler components, play a prominent part in the dyeing of hair. The developer components used are normally primary aromatic amines containing another free or substituted hydroxy or amino group in the para or ortho position, diaminopyridine derivatives, heterocyclic hydrazone derivatives, 4-amino-pyrazolone derivatives and tetraaminopyrimidines. Meta-phenylene diamine derivatives, phenols, naphthols, resorcinol derivatives and pyrazolones are used as couplers.

Good oxidation dye precursors must satisfy all the following requirements. They must form the required shades with sufficient intensity during the oxidative coupling reaction. These shades must show adequate stability to heat, light and chemicals, for example to the reducing agents used in the permanent waving of hair. In addition, oxidation dye precursors must also be readily absorbed by human hair without excessively staining the scalp and should be safe to use from the toxicological and dermatological viewpoint.

The above requirements are not satisfactorily fulfilled by the couplers currently used in oxidation hair dyes, particularly those couplers which form blue shades with known developers, such as p-tolylene diamine. The toxicological properties of many couplers, for example of the aromatic diamine type, are particularly problematical. Other couplers give dye finishes with unsatisfactory fastness properties.

The use of 4-chloro-3-aminophenol as a coupler in oxidation hair dyes is known from British patent application No. 1,530,686 and corresponding published German patent application No. 25 09 152. The use of chloromethyl-3-aminophenols containing chlorine or a methyl group in the 2-position as couplers in oxidation hair dyes is known from published German patent application No. 30 16 008. Finally, the use of 2-amino 4-hydroxy-5-chlorotoluene as a coupling component for developers of the aromatic p-diamine type is known from U.S. Pat Nos. 3,591,323; 4,031,160; and 4,101,576, as well as corresponding published German patent application No. 15 43 808. U.S. Pat. No. 4,031,160 also discloses an unsubstituted 6-chloro-4-methyl-3-aminophenol (2-amino-4-hydroxy-5-chlorotoluene). However, the hair dye finishes obtainable with known m-aminophenols as couplers are unsatisfactory in their fastness properties.

DESCRIPTION OF THE INVENTION

Other than in the operating examples, or where otherwise indicated, all numbers expressing quantities of ingredients or reaction conditions used herein are to be understood as modified in all instances by the term "about."

It has now been found that 2-methyl-4-chloro- (-5-aminophenol and derivatives thereof containing a lower alkyl group or a hydroxyalkyl group on the N-atom are suitable as couplers for producing oxidation hair dyes that are particularly fast to light and rubbing. The above-mentioned m-aminophenols are not known from the literature.

Accordingly, the present invention relates to new m-aminophenols corresponding to the following general formula

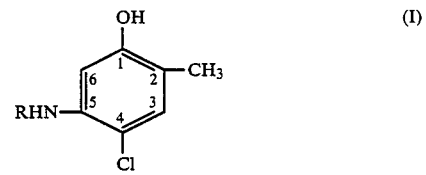

in which R represents hydrogen, a $C_{1-4}$ alkyl or a $C_{2-4}$ hydroxyalkyl, as well as water-soluble salts thereof.

The new m-aminophenols are produced from 4-chloro -2-methyl-5-nitrophenol, which is known from published British patent application No. 1,100,219, by catalytic hydrogenation to 4-chloro-2-methyl-5-aminophenol. To produce the aminophenols according to the invention corresponding to formula I, in which R is an alkyl or hydroxyalkyl moiety, the R substituent may be introduced in known manner. For example, alkyl may be introduced by alkylation, such as with an alkyl halide, especially an iodide corresponding to formula RI. The 2-hydroxyethyl may be introduced by initially introducing a 2-chloropropionyl on the nitrogen by acylation with chloroformic acid-2-chloroethylester, cyclizing it to 1,3-oxazolidin-2-one and, finally, hydrolyzing the 1,3-oxazolidin-2-one to N-(2-hydroxyethyl).

4-chloro-2-methyl-5-aminophenol is preferred, particularly by virtue of its ready availability. However, particularly light-fast dye finishes are also obtained with 4-chloro-2-methyl-5-(2-hydroxyethyl)-aminophenol.

The m-aminophenols according to the invention may be prepared and used both in free form and also in the form of their water-soluble salts, for example as hydrochlorides, sulfates, phosphates, acetate, propionates, lactates, citrates, or their compatible mixtures.

The present invention also relates to the use of the new m-aminophenols corresponding to general formula I, or salts thereof, as couplers together with standard developers in oxidation hair dyes.

The new couplers according to the invention are suitable for a number of different developer systems. They produce deep blue, violet, red or brown shades on the hair, depending on the developer used. The at least one m-aminophenol according to the invention is preferably used with at least one developer from the group comprising p-phenylene diamine, p-tolylene diamine, p-aminophenol or 2,4,5,6-tetraaminopyrimidine.

Compared with 2-methyl-5-aminophenol, the couplers according to the invention have the unexpected advantage of greater stability in the cream base particularly at elevated temperature (during incorporation in and during preparation of the dye creams).

The present invention also relates to hair dyes containing oxidation dye precursors in a cosmetic carrier, characterized in that they contain at least one coupler of general formula I in a quantity of from 0.05 to 10 millimoles per 100 g of the hair dye and at least one standard developer as oxidation dye precursors. The hair dyes according to the invention preferably also contain the abovementioned developers, namely p-phenylene diamine, p-tolylene diamine, p-aminophenol and/or 2,4,5,6-tetraaminopyrimidine. In addition, the hair dyes according to the invention may contain at least one other known developer, for example derivatives of the preferred developers mentioned above, diaminopyridine derivatives, heterocyclic hydrazone derivatives and 4-aminopyrazolone derivatives, and other known couplers, such as for example m-phenylene diamines, 2,4-diaminophenol ethers, phenols, naphthols, resorcinol derivatives, for example 2-methylresorcinol or pyrazolones.

At least one substantive dye may also be additionally used for further modifying the shades. Suitable substantive dyes are, for example, nitrophenylene diamines, nitroaminophenols, anthraquinone dyes or indophenols.

In the hair dyes according to the invention, the maminophenols corresponding to general formula I and the couplers additionally present, if any, are generally used in substantially molar quantities, based on the developers used. Although it has proved to be best to use substantially molar quantities, a certain excess of individual oxidation dye precursors is not a disadvantage, so that developers and couplers may be present in a molar ratio of 1:0.5–2.

In principle, the oxidative development of the dye may be carried out with atmospheric oxygen. However, it is preferred to use a chemical oxidizing agent, particularly when it is desired to lighten as well as dye the hair. Suitable oxidizing agents are, in particular, hydrogen peroxide or adducts thereof with urea, melamine or sodium borate and also mixtures of hydrogen peroxide adducts such as these with potassium peroxide disulfate.

To produce the hair dyes according to the invention, the oxidation dye precursors are incorporated in a suitable cosmetic carrier. Examples of suitable cosmetic carriers are creams, emulsions, gels, surfactant-containing foaming solutions, for example shampoos, or other preparations which are suitable for application to the hair. Standard ingredients of cosmetic preparations such as these are wetting agents and emulsifiers, such as anionic, nonionic or ampholytic surfactants, including soaps, fatty alcohol sulfates, alkane sulfonates, alpha-olefin sulfonates, fatty alcohol polyglycolether sulfates, ethylene oxide adducts with fatty alcohols, fatty acids and alkylphenols, sorbitan fatty acid esters and fatty acid partial glycerides, fatty acid alkanolamides, thickeners such as methyl or hydroxyethyl cellulose, starch, fatty alcohols, paraffin oils, fatty acids, as well as perfume oils and hair-care additives such as water-soluble cationic polymers, protein derivatives, pantothenic acid and cholesterol.

The ingredients of the cosmetic carriers are used in the usual quantities in the production of the hair dyes according to the invention. For example, the emulsifiers are used in concentrations of from 0.5 to 30% by weight and the thickeners in concentrations of from 0.1 to 25% by weight. The oxidation dye precursors are incorporated in the carrier in quantities of from 0.2 to 5% by weight and preferably in quantities of from 1 to 3% by weight, all of the foregoing percentages by weight being based upon the entire composition containing the inventive dye.

The hair dyes according to the invention may be used in a mildly acidic, neutral or alkaline medium, irrespective of the type of cosmetic preparation used. The hair dyes are preferably used at a pH of 8 to 10 and at temperatures of 15° C. to 40° C. After a contact time of around 30 minutes the hair dye is removed by rinsing from the hair to be dyed. The hair is then washed with a mild shampoo and dried. Washing with a shampoo is unnecessary when a carrier of high surfactant content, for example a dye shampoo, is used.

The hair dye finishes obtainable with the hair dyes according to the invention are characterized by high brilliance and by high fastness to heat, light, washing and rubbing.

The following Examples are intended to illustrate the invention without limiting it in any way.

EXAMPLES 1. 2-methyl-4-chloro-5-aminophenolhydrochloride (novel compound)

5 g of 4-chloro-2-methyl-5-nitrophenol were dissolved in 200 ml of ethanol and, after addition of 0.5 g of Raney nickel, the resulting solution was catalytically hydrogenated. When the uptake of hydrogen stopped, the catalyst was separated off by filtration and the filtrate acidified with dilute hydrochloric acid. Concentration to dryness produced light beige crystals melting at 198° C. (with decomposition).

2. 2-methyl-4-chloro-5-ethylaminophenol (novel compound)

A mixture of 3 g of 4-chloro-2-methyl-5-aminophenol (0.016 mol), 2.6 g of ethyliodide (0.017 mol), 1.35 g of sodium hydrogen carbonate (0.016 mol) and 30 ml of ethanol was refluxed for 7 hours. After cooling and dilution with 50 ml of water, the solution was neutralized with a sodium hydrogen carbonate solution and then extracted three times with 50 ml of ethylacetate. The extract was dried over sodium sulfate and concentrated to dryness. The residue was recrystallized from toluene. Beige crystals melting at 205° C. were obtained.

3. 2-methyl-4-chloro-5-(2-hydroxyethyl)-aminophenol (novel compound)

(a)
[beta-chloroethyl-(2'-chloro-4'-methyl-5'-hydroxy)-phenyl]-carbamate.

9.7 g of 2-methyl-4-chloro-5-aminophenolhydrochloride (0.05 mol) were suspended in 25 ml of dioxane. 5.5 g of calcium carbonate (0.055 mol) were then added and the temperature increased to +90° C. 7.9 g of chloroformic acid-2-chloroethylester (0.055 mol) were then added dropwise with stirring, followed by stirring for 1 hour at 90° C. The mixture was then cooled to 20° C. and separated off from the mineral salts by filtration. 100 ml of water were added to the filtered solution and the deposit forming was separated off by filtration. Beige crystals melting at 124° C. were obtained.

(b) N-[(2'chloro-4'-methyl-5'-hydroxy)-phenyl]-1,3 oxazolidin-2-one 10.6 g of the compound according to 3a (0.04 mol) were introduced into 24 ml of 4.3-molar sodium hydroxide at 45° C. After stirring for 20 minutes, ice water was added to the reaction mixture which was then neutralized with dilute hydrochloric acid. The desired product precipitated, was separated off by filtration and dried at 70° C. Beige crystals melting at 198° to 200° C. were obtained.

(c) 2-methyl-4-chloro-5-(2-hydroxyethyl)-aminophenol 7.3 g of the compound according to 3b (0.032 mol) were introduced into 20 ml of 5-molar sodium hydroxide at 70° C. After a reaction time of 30 minutes, the solution was cooled to 0° C. and neutralized with concentrated acetic acid. The product precipitating was separated off by filtration and dried at 70° C. Brown crystals melting at 111° C. (with decomposition) were obtained.

PERFORMANCE TESTS

In order to test the new couplers according to Examples 1 to 3, they were used in hair dye cream emulsions having the following composition:

| | |
|---|---|
| $C_{12-18}$ fatty alcohol | 10 g |
| $C_{12-14}$ fatty alcohol + 2 E.O. sulfate, Na salt (28%) | 25 g |
| Water | 60 g |
| Developer | 0.075 mol |
| Coupler | 0.075 mol |
| Inhibitor ($Na_2SO_3$) | 1.0 g |
| Concentrated ammonia solution | to pH 9.5 |
| Water | q.s. to 100 g |

The constituents were mixed together in the above order. After addition of the developer and the coupler, the pH value of the emulsion was first adjusted to 9.5 with concentrated ammonia solution, after which the emulsion was made up with water to 100 g.

The oxidative coupling was carried out with 3% hydrogen peroxide solution as oxidizing agent. To this end, 5 g of hydrogen peroxide solution (3%) were added to and mixed with 10 g of the dye cream.

The dye cream was applied to standardized, 90% gray, but not specially pretreated human hair and left thereon for 30 minutes at 35° C. After dyeing, the hair was rinsed, washed with a standard shampoo and then dried.

The following standard developer compounds were used:
 D 1: p-phenylene diamine
 D 2: p-tolylene diamine
 D 3: 2-chloro-p-phenylene diamine
 D 4: 2,5-diaminoanisole
 D 5: N-benzyl-p-phenylene diamine
 D 6: N-(2-hydroxypropyl)-p-phenylene diamine
 D 7: N-(p-aminophenyl)-N',N'-bis-(2-hydroxyethyl)-1,3-diaminopropane
 D 8: N,N-dimethyl-p-phenylene diamine
 D 9: N,N-bis-(2-hydroxyethyl)-p-phenylene diamine
 D 10: 2,5-diaminobenzylalcohol
 D 11: N-methyl-p-phenylene diamine
 D 12: N-(2-hydroxyethyl)-p-phenylene diamine
 D 13: N-(2-methoxyethyl)-p-phenylene diamine
 D 14: N-butyl-N-sulfobutyl-p-phenylene diamine
 D 15: N,N-diethyl-p-phenylene diamine
 D 16: N-ethyl-N-(2-hydroxyethyl)-p-phenylene diamine
 D 17: 2,5-diaminopyridine
 D 18: p-aminophenol
 D 19: 2,4,5,6-tetraaminopyrimidine
 D 20: 2-dimethylamino-4,5,6-triaminopyrimidine.

The following novel inventive compounds were used as couplers:

C 1: 2-methyl-4-chloro-5-aminophenolhydrochloride
 C 2: 2-methyl-4-chloro-5-ethylaminophenol
 C 3: 2-methyl-4-chloro-5-(2-hydroxyethyl)-aminophenol.

The colors of the dye finishes obtained are shown in Table I.

The following couplers are known from published Germany patent application No. 30 16 008 and were used in comparison tests for testing the light fastness properties of the dye finishes:
 CC 4: 2-chloro-6-methyl-3-aminophenol
 CC 5: 2-methyl-6-chloro-3-aminophenol.

TESTING OF LIGHT FASTNESS

The fastness to light of the dyed hair strands was determined in accordance with German Industrial Norm (DIN) 54,004 (April 1966), Section 7.5.2. The method essentially comprises exposing the dyed hair strands alongside fabric samples with 8 blue standard dyes of the fastness scale graduated in their fastness to light, to the light of a xenon arc lamp with a color temperature of 5,500° to 6,500° C. K. To this end, the strands and fabric samples are fastened alongside one another to a card and the marginal zones of the strands and fabric samples are covered parallel to the longitudinal edge of the sample holder. Exposure is carried out with frequent inspection by removal of the cover plate until standard 3 of the light fastness scale shows a just noticeable difference between the exposed part and the unexposed part. The samples are then inspected for changes and the changes, if any, are evaluated by comparison with the changes in standards 1, 2 and 3 of the fastness scale. Exposure is then continued until standard 4 of the light fastness scale also shows a just noticeable difference in color between the exposed part and the unexposed part. The cover plate is then replaced by a larger cover plate which covers approximately ⅓ of the previously exposed surface parallel to the longitudinal edge. Exposure is then continued until standard 6 of the scale shows a just noticeable color difference. Light fastness is determined by comparing the contrast on the strands of hair with the contrasts on the standard dye finishes of the light fastness scale.

The results of these light fastness tests are shown in Table II:

TABLE I

| Example | Developer | Coupler | Color of the colored hair |
|---|---|---|---|
| P 1 | D 1 | C 1 | gray-green |
| P 2 | D 2 | C 1 | dark violet |
| P 3 | D 2 | C 2 | dark purple |
| P 4 | D 2 | C 3 | violet |
| P 5 | D 3 | C 1 | dark ruby |
| P 6 | D 4 | C 1 | dark violet |
| P 7 | D 5 | C 1 | dark violet |
| P 8 | D 6 | C 1 | dark violet |
| P 9 | D 7 | C 1 | dark purple |
| P 10 | D 8 | C 1 | dark violet |
| P 11 | D 9 | C 1 | dark violet |
| P 12 | D 10 | C 1 | dark magenta |
| P 13 | D 11 | C 1 | dark violet |
| P 14 | D 12 | C 1 | dark violet |
| P 15 | D 13 | C 1 | dark violet |
| P 16 | D 14 | C 1 | gray-violet |
| P 17 | D 15 | C 1 | dark violet |
| P 18 | D 16 | C 1 | dark violet |
| P 19 | D 17 | C 1 | gray-brown |
| P 20 | D 18 | C 1 | red-brown |
| P 21 | D 19 | C 1 | dull violet |
| P 22 | D 20 | C 1 | dark blue |

TABLE II

| Example | Developer | Coupler | Color | Light fastness rating |
|---------|-----------|---------|-------|-----------------------|
| V 1 | D 2 | C 1 | dark violet | 6 |
| V 2 | D 2 | CC 4 | blue-violet | 5 |
| V 3 | D 2 | CC 5 | dark violet | 4 |

We claim:

1. A meta-aminophenol compound of the formula:

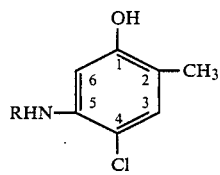

wherein: R is H, a $C_{1-4}$-alkyl, or a $C_{2-4}$-hydroxyalkyl; or a water-soluble salt thereof.

2. The compound of claim 1 wherein R is H.
3. The compound of claim 1 wherein R is $C_1$-alkyl.
4. The compound of claim 1 wherein R is $C_2$-alkyl.
5. The compound of claim 1 wherein R is $C_3$-alkyl.
6. The compound of claim 1 wherein R is $C_4$-alkyl.
7. The compound of claim 1 wherein R is $C_2$-hydroxyalkyl.
8. The compound of claim 1 wherein R is $C_3$-hydroxyalkyl.
9. The compound of claim 1 wherein R is $C_4$-hydroxyalkyl.
10. The compound of claim 1 in the form of a water soluble salt which is at least one hydrochloride, sulfate, phosphate, acetate, propionate, lactate, or citrate.
11. In an oxidation hair dye comprising as its coloring components at least one coupler and at least one developer selected from the group consisting of p-phenylene diamine, p-tolylene diamine, and mixtures thereof in a mole ratio of 1:0.5–2, the improvement wherein said at least one coupler consists essentially of a meta-aminophenol compound of the formula

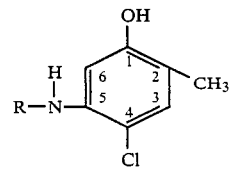

wherein R is H, a $C_{1-4}$ alkyl group, or a $C_{2-4}$ hydroxyalkyl group; or a water-soluble salt thereof.

12. The oxidation hair dye of claim 11 wherein said developer is p-phenylene diamine.
13. The oxidation hair dye of claim 11 wherein said coupler is:
2-methyl-4-chloro-5-aminophenolhydrochloride;
2-methyl-4-chloro-5-ethylaminophenol;
2-methyl-4-chloro-5-(2-hydroxyethyl)-aminophenol; or any mixture thereof.
14. The oxidation hair dye of claim 12 wherein said coupler is:
2-methyl-4-chloro-5-aminophenolhydrochloride;
2-methyl-4-chloro-5-ethylaminophenol;
2-methyl-4-chloro-5-(2-hydroxyethyl)-aminophenol; or any mixture thereof.
15. The oxidation hair dye of claim 11 incorporated within a cosmetic carrier, wherein said dye is present in a quantity of 0.2 to 5% by weight, based upon the weight of the total cosmetic-dye composition.
16. The cosmetic-oxidation hair dye composition of claim 15 wherein said at least one coupler is present in 0.05 to 10 millimols per 100 g of oxidation hair dye.

* * * * *